US00PP28082P2

(12) United States Plant Patent
Kinney

(10) Patent No.: US PP28,082 P2
(45) Date of Patent: Jun. 6, 2017

(54) ***JUNIPERUS* PLANT NAMED 'MONGEO'**

(50) Latin Name: *Juniperus horizontalis*
Varietal Denomination: MonGeo

(71) Applicant: Ron D. Kinney, Dayton, OR (US)

(72) Inventor: Ron D. Kinney, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 5 days.

(21) Appl. No.: 14/757,214

(22) Filed: Dec. 4, 2015

(51) Int. Cl.
*A01H 5/08* (2006.01)

(52) U.S. Cl.
USPC ..... Plt./214

(58) Field of Classification Search
USPC ..... Plt./214
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Juniperus* cultivar named 'MonGeo' is disclosed, characterized by distinctive Yellow 5A foliage patches and Greyed-Purple winter foliage. The new cultivar is a *Juniperus horizaontalis*, suitable for ornamental garden purposes.

3 Drawing Sheets

Latin name of the genus and species: *Juniperus horizontalis*.

Variety denomination: 'MonGeo'.

BACKGROUND OF THE INVENTION

The new cultivar is a product of chance discovery by the inventor, Ron D. Kinney. This new variety, hereinafter referred to as 'MonGeo', was selected as a naturally occurring single branch mutation of the unpatented *Juniperus horizontalis* 'Youngstown'. The novel new variety was discovered in a commercial nursery in Dayton, Oreg. during September of 2008.

After identifying the new variety as a potentially interesting selection, the inventor first organized propagation of 'MonGeo' by semi-hardwood cuttings at the same commercial nursery during September of 2008. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'MonGeo' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonGeo' These characteristics in combination distinguish 'MonGeo' as a new and distinct *Juniperus* cultivar:

1. Unique color of foliage:
   Spring, Summer and Fall foliage is green with significant Yellow 5A coloration throughout plant.
   Green foliage turns near Greyed-Purple N187B and N187C in Winter.
   Yellow coloration is maintained during Winter.

COMPARISON TO PARENT VARIETY

'MonGeo' is similar in most horticultural characteristics to the parent variety. Plants of the new cultivar 'MonGeo' however, produce distinctive foliage colored in large patches near Yellow 5A, whereas the parent variety has solid green foliage. Additionally, the new variety changes foliage color in the Winter to Greyed-Purple, whereas the parent variety does not.

COMMERCIAL COMPARISON

In addition to the parent, 'MonGeo' can be compared to the commercial variety *Juniperus horizontalis* 'Blue Chip', unpatented. The varieties are similar in most horticultural characteristics, however, plants of 'MonGeo' produce Winter foliage significantly colored Greyed-Purple, whereas plants of 'Blue Chip' produce a faint Greyed-Purple coloration in Winter. Additionally, plants of the new variety grow approximately two feet wider on average and have Yellow 5A foliage coloration not found in this comparator.

'MonGeo' can be compared to the commercial variety Juniperus horizontalis 'Andorra Variegata', unpatented. The varieties are similar in most horticultural characteristics, including both having yellow patches of foliage. However, plants of the new variety differ in the following characteristics:

1. Yellow foliage patches of the new variety are darker and brighter, Yellow 5A, compared to near Yellow 10D foliage patches of 'Andorra Variegata'.
2. Winter color of the new variety is Greyed-Purple with Yellow 5A patches. Winter color of 'Andorra Variegata' is Greyed-Red with yellow 10D patches.
3. Plants of the new variety grow 2 to 3 feet wider than plants of this comparator.

BRIEF DESCRIPTION OF THE PHOTOGRAPHS

The accompanying photograph in FIG. 1 illustrates in full color a typical plant of 'MonGeo' grown outdoors in Dayton, Oreg. The plant is approximately 2 years old, and is shown in a three gallon container.

Figure 1:
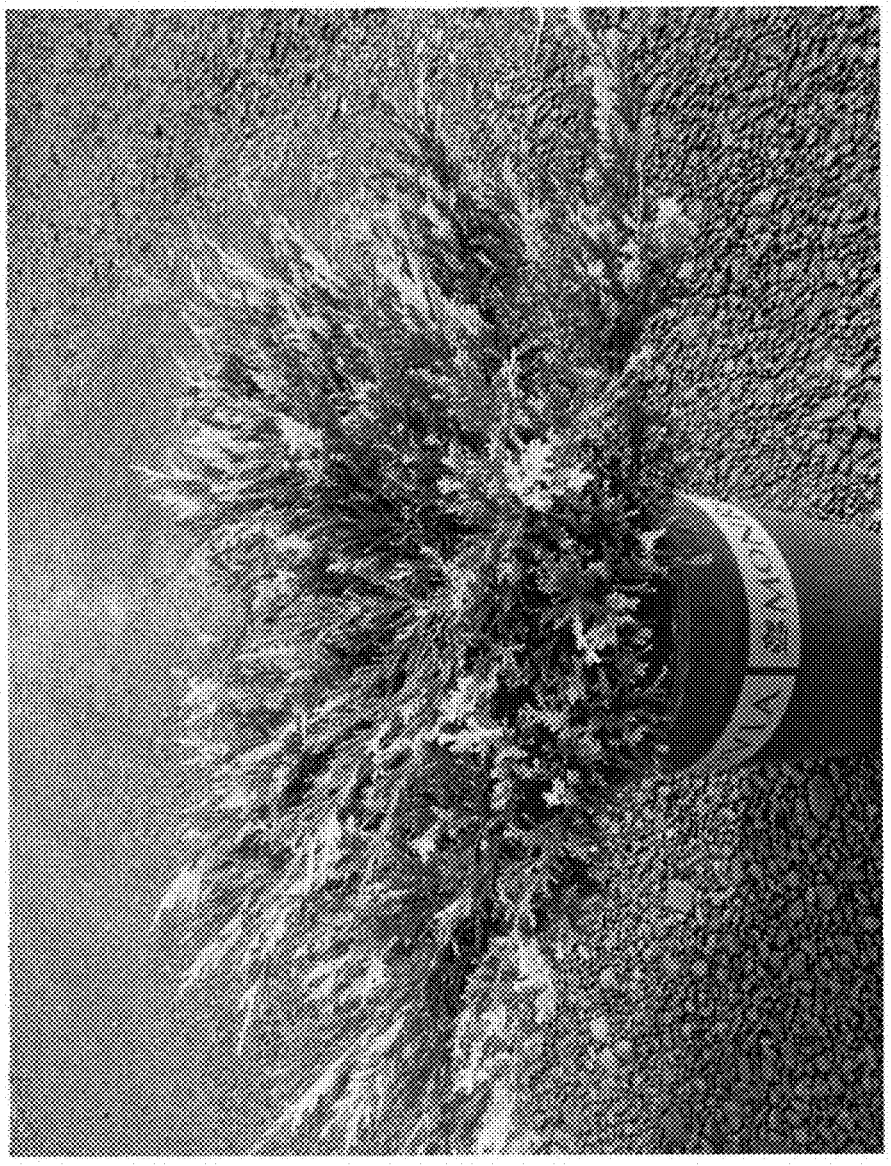
Figure 2:
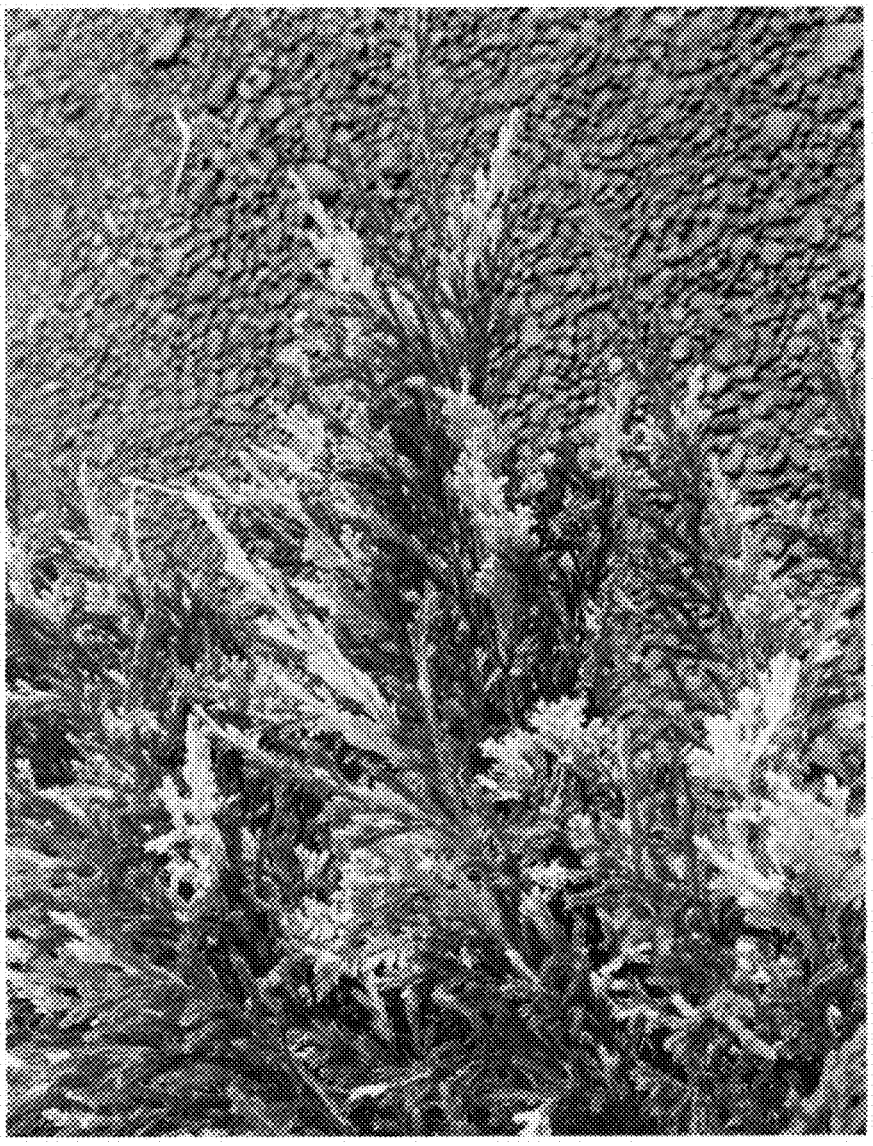
FIG. 2 illustrates a close up of a branch of the new variety, with Yellow patches of color.
Figure 3:
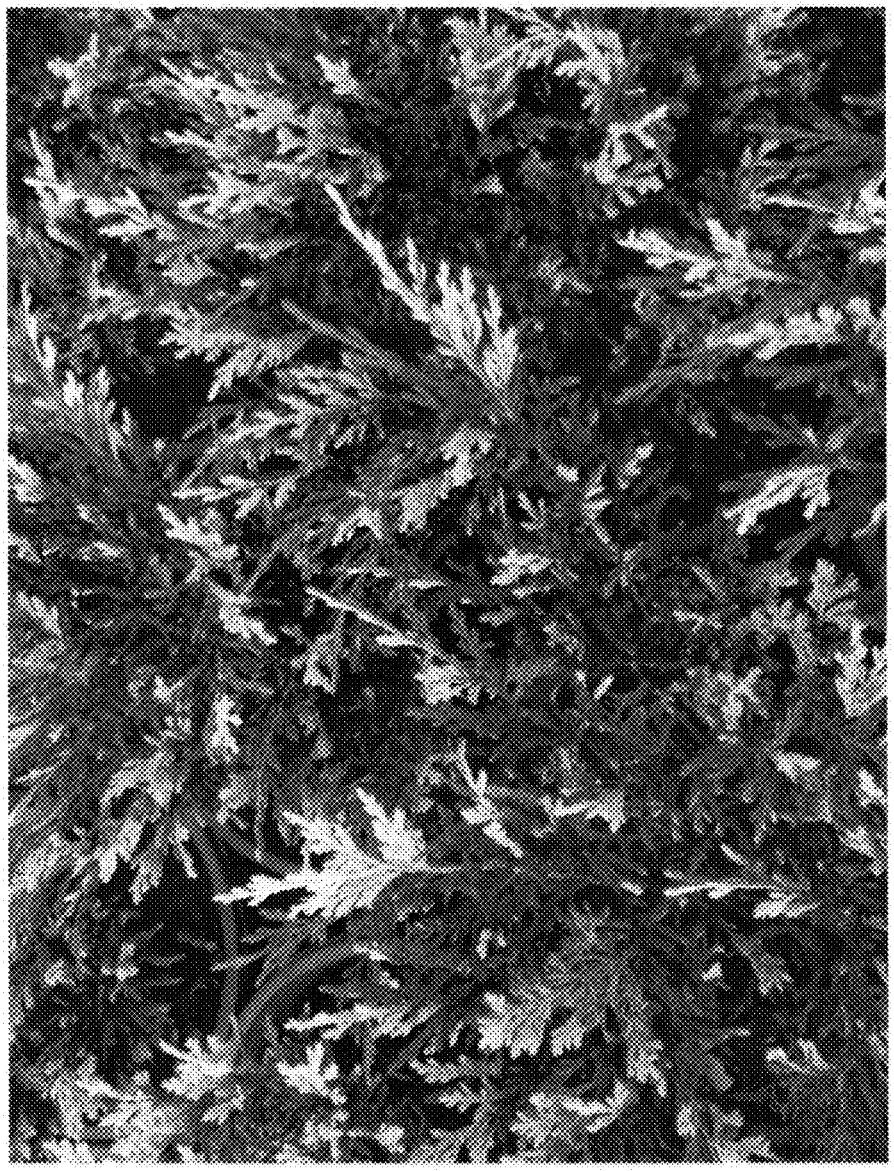
FIG. 3 illustrates the Winter Foliage color.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonGeo' plants grown outdoors in Dayton, Oreg. Plants are approximately 1 year old, in a 1 gallon nursery container. Measurements and numerical values represent averages of typical plant types.

Botanical classification: *Juniperus horizontalis* 'MonGeo'.

PROPAGATION

Time to rooting: About 90 days at approximately 20° C.

Time to produce a rooted cutting: Approximately 200 days.

Root description: Fibrous, moderately well branched. Colored near RHS Brown 200C and Near Orange-White 159D.

PLANT

Growth habit: Evergreen semi-prostrate woody shrub.

Height: Approximately 20 cm. after 1 year.

Plant spread: Approximately 40 cm. after 1 year.

Typical growth rate: Moderate for species.

Branching characteristics: Approximately 3 to 4 main stems with approximately 6 to 12 lateral branches. Lateral stems are held at an angle of approximately 30 to 45 degree from the main stem.

Stems:

- *Length*.—Average 15 to 18 cm.
- *Diameter*.—0.7 cm.
- *Color*.—Near RHS Grey-Brown 199A.
- *Texture*.—Rough, scaly.
- *Strength*.—Very strong and flexible.

Lateral branches:

- *Length of lateral branches*.—Average range 8 to 14 cm.

Diameter of lateral branches: Average 0.4 cm.

Lateral branch shape in cross section: Round.

Lateral branch strength: Flexible, strong.

Lateral branch color: Near RHS Yellow-Green 145B.

Lateral branch texture: Smooth, covered with foliar scales. Scales Needle-like, average length 8 mm, diameter 1 mm. Colored near RHS Green 138A.

Internode length: Average range between 0.5 cm and 1.0 cm.

FOLIAGE

General description: Needle-like, imbricate, slightly appressed.

Leaf:

- *Arrangement*.—Alternate and whorled.
- *Type*.—Simple, needle-like.
- *Shape of blade*.—Linear.
- *Average length*.—Approximately 5 mm.
- *Average width*.—Approximately 1 mm.
- *Apex*.—Acute.
- *Base*.—Obtuse.
- *Attachment*.—Sessile.
- *Margin*.—Entire.
- *Texture of top surface*.—Glabrous.
- *Texture of bottom surface*.—Glabrous.
- *Leaf internode length*.—Less than 1 mm.
- *Color*.—Young foliage upper side: Near RHS Green 138A. Young foliage under Near RHS Green 138A. Young foliage Yellow Patches: Near RHS Yellow 5A. Mature foliage upper side: Near RHS Green 137B. Mature foliage under side: Near RHS Green 137B. Mature foliage Yellow Patches: Near RHS Yellow 5A.

Winter foliage:

- *Upper side*.—Near RHS Greyed-Purple N187A and N187B.
- *Under side*.—Near RHS Greyed-Purple N187A and N187B. Yellow patches in Winter: Near RHS Yellow 5A.
- *Venation*.—Linear, indistinguishable from leaf blade.
- *Durability of foliage to stresses*.—Flexible and resistant to breakage.
- *Fragrance*.—Moderate Juniper scent.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 3-9.

What is claimed is:

1. A new and distinct cultivar of *Juniperus* plant named 'MonGeo' as herein illustrated and described.

* * * * *